(12) United States Patent
Trucko

(10) Patent No.: US 7,351,312 B1
(45) Date of Patent: Apr. 1, 2008

(54) APPARATUS FOR OBTAINING SAMPLE AND PROCESS THEREFOR

(75) Inventor: Jessy E. Trucko, Glendale Heights, IL (US)

(73) Assignee: UOP LLC, Des Plaines, IL (US)

( * ) Notice: Subject to any disclaimer, the term of this patent is extended or adjusted under 35 U.S.C. 154(b) by 450 days.

(21) Appl. No.: 10/738,581

(22) Filed: Dec. 17, 2003

(51) Int. Cl.
*B01D 3/14* (2006.01)
*G01N 25/14* (2006.01)

(52) U.S. Cl. ............... 203/88; 73/61.77; 73/863.12; 159/2.1; 203/100

(58) Field of Classification Search ............... 203/1.88, 203/100; 202/185.1; 159/2.1; 73/61.77, 73/863, 863.12; 95/209, 211; 261/DIG. 72
See application file for complete search history.

(56) References Cited

U.S. PATENT DOCUMENTS

| 2,459,550 | A | * | 1/1949 | Stamm ........................ 201/11 |
| 2,530,376 | A | * | 11/1950 | Castle et al. ................ 202/187 |
| 3,274,076 | A | * | 9/1966 | Watt ........................... 202/187 |
| 3,382,649 | A | * | 5/1968 | Richmond .................... 95/227 |
| 3,391,577 | A | * | 7/1968 | Friauf et al. ............. 73/863.12 |
| 3,668,825 | A | * | 6/1972 | McIlvaine ........................ 95/8 |
| 3,953,298 | A | * | 4/1976 | Hogan ........................ 196/133 |
| 4,390,500 | A | * | 6/1983 | Miskinis ..................... 422/103 |
| 4,495,032 | A | * | 1/1985 | Everman ..................... 202/105 |
| 4,854,180 | A | * | 8/1989 | Mauleon et al. ......... 73/863.86 |
| 5,078,758 | A | * | 1/1992 | Maller et al. ................. 95/211 |
| 5,134,879 | A | * | 8/1992 | Wong et al. ................ 73/61.72 |
| 5,154,061 | A | * | 10/1992 | Weisshaar .................... 62/606 |
| 6,769,487 | B2 | * | 8/2004 | Hache ........................ 166/302 |
| 7,109,328 | B2 | * | 9/2006 | Hammon et al. ............. 544/35 |
| 2005/0006219 | A1 | * | 1/2005 | Eck et al. ....................... 203/1 |

* cited by examiner

*Primary Examiner*—Virginia Manoharan
(74) *Attorney, Agent, or Firm*—James C Paschall

(57) ABSTRACT

A vessel is provided for collecting a process stream and fractionating the process stream into a liquid and gas phase in the vessel. Cooling may be provided by an internal bath and/or an external bath. The liquid phase retained in the vessel and the gas phase collected in lots from the vessel may be delivered to a lab for analysis.

15 Claims, 1 Drawing Sheet

APPARATUS FOR OBTAINING SAMPLE AND PROCESS THEREFOR

BACKGROUND OF THE INVENTION

This invention relates to an apparatus for collecting a sample from an on-stream process and a method for using the apparatus. Specifically, the apparatus collects a hydrocarbon sample from an on-stream chemical process and provides a separation between lighter and heavier materials.

DESCRIPTION OF THE PRIOR ART

A variety of sampling containers are available for taking samples of products or process intermediates from an on-stream chemical process to analyze sample composition. The composition of product and intermediate process streams are analyzed to assess process performance. It is most useful to take these samples while the process is operating to more accurately assess performance.

The fluidized catalytic cracking (FCC) process is an example of a chemical process from which on-stream samples are taken to assess performance. To take samples from a live FCC process, samples are drawn from a process stream conduit through copper or stainless steel tubing and collected in 100-liter, gas-tight bags. Travel through the tubing cools the sample stream. The bags may be stored for a period of time allowing the sample to reach room temperature and establish vapor-liquid equilibrium. The samples may then be pulled from the bags into, for example, an aluminum sample vessel by a vacuum while samples of the off-gas are taken at regular intervals and collected in glass sample cylinders, for example. The aluminum sample vessel and glass sample cylinders are then shipped off-site to a laboratory for analysis. During analysis, the contents of the aluminum sample vessel are each cooled to freeze the water in the sample and the oil decanted off and combined to obtain a hydrocarbon oil of analyzable volume.

In the current environment, refiners who are endeavoring to provide clean fuels are interested in the concentrations of sulfur compounds, olefins and dienes in process streams. However, the copper or steel tubing using for collecting samples of process streams is catalytically active and chemically reactive with sulfur compounds, olefins and dienes. Multiple transfer, weighing and handling steps expose the sample to oxygen which is also reactive with these compounds. Hence, the accuracy of speciation and quantification results is diminished.

Collecting samples at ambient conditions reduces retention of the liquid component of the process stream which evaporates into the gas phase. Hence, analysis of the heavy portion of the process stream is limited.

Accordingly, it is an object of this invention to obtain samples of process streams with no contact with catalytic material or reactive species to provide unadulterated samples. It is an additional object of this invention to obtain samples of process streams in a portable vessel which cuts the sample into lighter and heavier fractions.

BRIEF SUMMARY OF THE INVENTION

We have designed an apparatus and process for collecting samples of process streams that prevents exposure to reactive species and provides an integral fractionation between lighter and heavier materials. An adequate volume of liquid may be retained for analysis.

Additional objects, embodiments, and details of this invention are given in the following detailed description of the invention.

DETAILED DESCRIPTION OF THE INVENTION

Figures 1, 2:
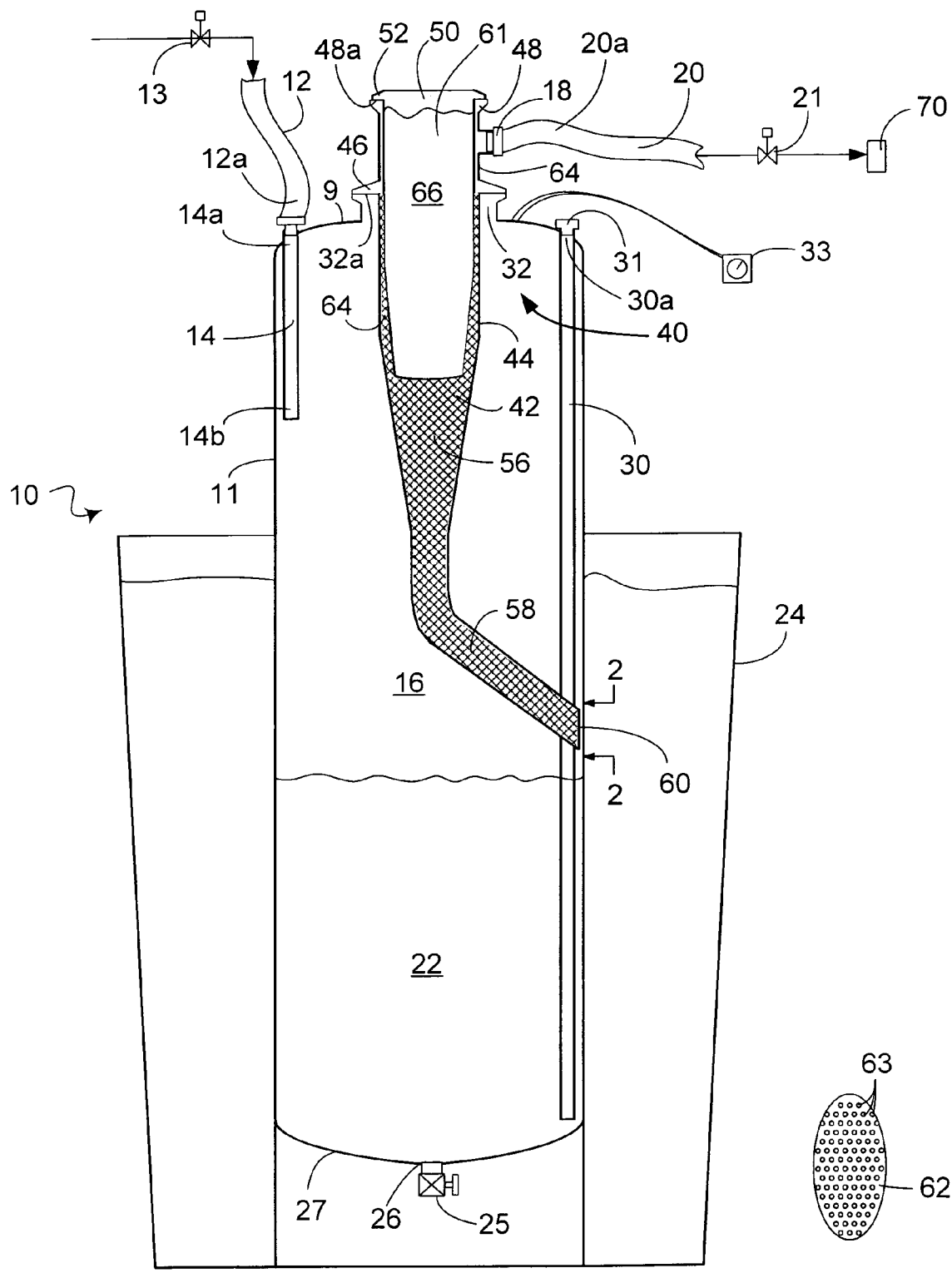
FIG. 1 shows a sectional elevation view of an apparatus for obtaining a sample of a process stream.
FIG. 2 is an elevational view taken along segment 2-2 in FIG. 1

FIG. 1 sectionally shows a vessel 10 for collecting a sample from a live process stream. Several accoutrements such as handles and clamps are not shown to simplify the drawing and highlight the invention. Also not shown is a coating on the inner wall of all fluid carrying and holding components of an inert material to prevent reactivity with the sample fluid. SULFINERT available from Restek Corporation is a suitable coating to prevent reactivity with sulfur compounds, dienes and olefins. Even a transfer inlet line 12 that transports a sample stream to the vessel 10 has an inert coating on an inner wall thereof. The vessel 10 may be made of any suitable material that can withstand pressure and the temperature of the coating process which may be around 600° C. (1112° F.). Stainless steel with an inner surface coated with an inert material is suitable. The vessel 10 may comprise a cylindrical wall 11 with a hemispherical top 9 and a bottom 27.

The inlet line 12 or tube has an end (not shown) connectable to a process stream of a live chemical process unit such as an FCC unit (not shown) and the other end 12a fluidly connected to a short dip tube 14 through a top 9 of the vessel. An inlet end 14a of the dip tube may have female screw threads for facilitating connection to a male screw threaded end 12a of the inlet line 12. The sample fluid, which may be a stream of hydrocarbon, water or other species, enters the vessel 10 through the short dip tube 14 and flashes into an open volume 16 of the vessel 10 through an open lower end 14b of the short dip tube 14. Upon flashing, the sample fluid separates between liquid and gaseous phases. The liquid phase 22 will collect on the bottom of the vessel 10. The gas phase is withdrawn through a gas outlet 18 through a gas outlet tube 20. An inlet end 20a of the outlet tube may have male screw threads for facilitating connection to female screw threads in the gas outlet 18. A pressure regulator valve 21 on the gas outlet tube 20 may be used to regulate the pressure in the vessel 10. Moreover, the vessel 10 may be at least partially submerged in an ice water or other liquid bath 24 to cool the vessel 10. The inlet tube 12 and the outlet tube 20 may be made of stainless steel or other material as long as the inner surface is coated with an inert layer.

If the sample stream is taken from an FCC product stream, the cut between liquid and gases may be made such that C4 and lighter hydrocarbons are in the gas phase and C5 and heavier hydrocarbons are in the liquid phase. A temperature in the vessel 10 of below ambient temperature, such 4° to 10° C. (40° to 50° F.), and a pressure of 34.5 kPa (gauge) (5 psig) will operate to promote this desired split. The process stream from which the on-stream sample may be taken may include a feed stream, an intermediate product stream, a product effluent stream or a by-product stream.

A heavy liquid port 26 in the bottom 27 of the vessel 10 allows removal of heavy liquid phases. A male screw-threaded valve 25 in the female screw threaded port 26 can be opened to allow drainage of the heavy liquid phase. Water often present in hydrocarbon streams can be drained from the hydrocarbon and evaluated by this means. The bottom 27 is rounded or sloped to facilitate accumulation of the heavy liquid phase at the heavy liquid port 26 at the center of the bottom 27.

A long dip tube 30 may optionally be provided for access to the liquid phase 22. During operation, the inlet 30a to the dip tube may be pressure capped by a male screw-threaded plug 31 in the female screw threaded inlet 30a. Other ports (not shown) in the top 9, the bottom 27 or the wall 11 of the vessel 10 may be desirable. For example, a thermocouple well (not shown) may extend through an opening in the top 9 of the vessel. In an embodiment, a pressure gauge 33 or other indicator is mated with a port (not shown) in the top 9 of the vessel.

The sample vessel 10 includes an internal fractionation assembly in the nozzle 32 of the vessel 10. The nozzle 32 includes a flange 32a for supporting a funnel shaft 44. The funnel shaft 44 may be filled with packing such as Raschig rings to facilitate gas-liquid contacting and fractionation. A lower flange 46 of the funnel shaft is supported on the flange 32a of the nozzle 32. During operation, the two flanges 32a and 46 are clamped together to be pressure tight. A suitable clamping device is a Ladish flange (not shown). The top of the funnel shaft 44 defines a nozzle 48 that includes an upper flange 48a. A cup 50 is inserted into the nozzle 48 of the funnel shaft 44. A flange 52 on the cup 50 rests on the upper flange 48a to support the cup 50 in the nozzle 48 of the funnel shaft 44. During operation, the two flanges 48a and 52 are clamped together to be pressure tight. A suitable clamping device is a Ladish flange (not shown). The cup 50 and the funnel shaft 44 arc suitably made of metal such as stainless steel to facilitate pressurization and heat transfer. Both the inner and outer surfaces of the cup 50 and the funnel shaft 44 are coated with an inert material as previously mentioned to suppress reactivity and catalysis with the sample fluid. Moreover, an O-ring may be sealed in coincident grooves in the mated flanges 32a, 46 and 48a, 52 to further seal against pressure leaks. The middle section 56 of the funnel shaft 44 defines a frustocone which communicates with a lower dogleg tube 58. The dogleg tube 58 slopes downwardly to a lower port 60. The lower port 60 is downwardly spaced from the outlet 18. A perforated plate 62 shown in FIG. 2 regulates entry into and out of the lower port 60 but prevents the packing from falling out. The plate 62 includes the openings 63 that are too small to allow packing pieces from passing therethrough but allow passage of the gaseous phase. The lower port 60 into the funnel shaft 44 is doglegged or angled such as at 45 degrees to maximize tube length without descending into the liquid phase and to juxtapose the port 60 into the funnel shaft 44 with the wall of the vessel 10 which is proximate to the ice water bath 24. Additionally, the cup 50 provides a cooling reservoir 61 to hold a cooling substance 66 for further cooling the gaseous phase. A mixture of dry ice and acetone or ice and salt water may be suitable cooling substance, but the former is cooler. An annular passage 64 is defined between the outer surface of the cup 50 and the inner surface of the funnel shaft 44.

In operation, the gaseous phase of the sample stream flashed upon entry through inlet 14a into the open volume 16 is cooled in the vessel 10 because heat is withdrawn into the ice water bath 24. Heavier components of the gas phase condense upon cooling and transition into the liquid phase 22. A stream of the gaseous phase entering the port 60 is further cooled because it is routed close to the wall of the vessel 10 which conducts heat removal through the wall of the vessel 10 in contact with the ice water bath 24. Further condensation of remaining heavier components in the gas phase results upon entry into the funnel shaft 44 through the port 60. As the gas stream travels up the funnel shaft 44 through the packing further gas-liquid contacting occurs to fractionate out remaining heavier components. As the gas stream ascends through the annular passage 64, it is further cooled by heat removal conducted through the wall of the cup 50. Even further condensation of remaining heavier components in the gas stream occurs in the annular passage 64 before the gas stream is allowed to exit the vessel 10 through the gas outlet 18.

The sample vessel is used to take a sample by displacing all of the oxygen from the vessel 10 perhaps by pressuring it with an inert gas such as nitrogen on the inlet tube 12 and applying a vacuum on the outlet tube 20 to pull the nitrogen and oxygen with it out of the vessel 10. This may be done several times, perhaps five, to purge all of the oxygen. The vessel 10 is secured to the bottom of the ice water bath 24 to avoid buoyancy problems. The vessel 10 and the bath 24 should be situated on a weight scale to monitor retained sample weight attributed to the liquid phase. The dry ice and acetone bath or equivalent mixture is prepared in the cup 50. The pressure regulator valve 21 on the exit line 20 should be set to a pressure greater than the pressure of the process stream to be sampled. An inlet valve 13 on the inlet tube 12 is opened to allow fluid communication between the process stream through the inlet tube 12 and the vessel 10 until the pressure in the vessel builds to a predetermined pressure, such as 34.5 kPa (gauge) (5 psig). Then the pressure regulator valve 21 is reduced to the predetermined pressure to allow flow of the sample stream from the process stream into the vessel 10. Gas samples are collected periodically, such as every five to ten minutes, in an individual canister 70 with an inner surface coated with an inert layer. When the weight scale indicates that the desired amount of liquid phase is collected, flow of the process stream through the inlet tube 12 should be stopped by shutting of the inlet valve 13. The gas samples in the canisters 70 and the liquid phase in the vessel 10 may then be delivered to the lab for analysis.

The vessel is preferably made portable, so it can be easily ported to the lab. A vessel 10 of no more than about four feet high and no more than a foot in diameter may be suitable.

It is also contemplated that heat be applied to the vessel 10 instead of cooling the vessel 10. Other means of cooling or heating may be used than baths.

What is claimed is:

1. An apparatus for collecting a sample of a process stream comprising:
   a vessel including a top and at least one wall enclosing an open volume;
   an inlet to the vessel to allow a fluid sample stream to enter into said open volume and flash into liquid and gas phases;
   a shaft disposed in said vessel, said shaft including a gas outlet from the vessel and a port in communication with said vessel for said gas phase to enter said shaft to be fractionated; and
   a coolant reservoir disposed in said shaft proximate said gas outlet defining a passage between the coolant reservoir and the shaft through which said gas phase may travel to further condense lighter materials in said gas phase into said liquid phase.

2. The apparatus of claim 1 wherein the port of said shaft is vertically spaced from said gas outlet.

3. The apparatus of claim 2 wherein said shaft is disposed in a nozzle in the top of said vessel.

4. The apparatus of claim 2 wherein said shaft contains packing material.

5. The apparatus of claim 2 wherein said port of said shaft is disposed proximate to a wall of said vessel.

6. The apparatus of claim 1 wherein said vessel is situated in a coolant bath.

7. An apparatus for collecting a sample of a process stream comprising:

a vessel including a top and at least one wall enclosing an open volume;

an inlet to the vessel to allow a fluid sample stream to enter into said open volume and flash into liquid and gas phases;

a shaft disposed in a nozzle in the top of said vessel, said shaft including a gas outlet from the vessel and a gas port downwardly spaced from said gas outlet; and a coolant reservoir contained in said shaft proximate said gas outlet to further condense lighter materials in said gas phase traveling in a passageway between said coolant reservoir and said shaft into said liquid phase.

8. The apparatus of claim 7 wherein a gas port of said shaft is horizontally spaced from said gas outlet.

9. The apparatus of claim 7 wherein said shaft contains packing material.

10. The apparatus of claim 7 wherein an inlet of said shaft is disposed proximate to a wall of said vessel.

11. The apparatus of claim 7 wherein said vessel is situated in a coolant bath.

12. A process for collecting a sample from a process stream comprising:

flashing a stream of sample into an open volume of a vessel to separate a liquid phase from a gas phase;

collecting said liquid phase in said vessel;

fractionating said gaseous phase while passing through a shaft that includes an outlet from said vessel to condense heavier components out of said gaseous phase;

withdrawing said gaseous phase through said outlet from said vessel; and cooling said gaseous phase with a coolant reservoir contained in said shaft as it travels to said outlet to condense lighter materials from said gaseous phase.

13. The process of claim 12 wherein said shaft contains packing.

14. The process of claim 12 further including passing said gaseous phase into an inlet of said shaft proximate a wall of the vessel.

15. The process of claim 12 further including cooling the entire vessel in a bath.

* * * * *